United States Patent
Albertorio et al.

(10) Patent No.: US 9,101,461 B2
(45) Date of Patent: Aug. 11, 2015

(54) BUTTON AND CONTINUOUS LOOP FOR FIXATION OF LIGAMENTS

(75) Inventors: Ricardo Albertorio, Naples, FL (US); Tara Schaneville, Bonita Springs, FL (US); Brian S. Hallett, Somerset (GB)

(73) Assignee: Arthrex, Inc., Naples, FL (US)

( * ) Notice: Subject to any disclaimer, the term of this patent is extended or adjusted under 35 U.S.C. 154(b) by 1482 days.

(21) Appl. No.: 11/889,740

(22) Filed: Aug. 16, 2007

(65) Prior Publication Data
US 2008/0046009 A1    Feb. 21, 2008

Related U.S. Application Data

(60) Provisional application No. 60/837,937, filed on Aug. 16, 2006.

(51) Int. Cl.
*A61F 2/08* (2006.01)
*A61B 17/04* (2006.01)

(52) U.S. Cl.
CPC ........... *A61F 2/0811* (2013.01); *A61B 17/0401* (2013.01); *A61B 2017/0404* (2013.01); *A61B 2017/0458* (2013.01); *A61F 2002/0817* (2013.01); *A61F 2002/0847* (2013.01); *A61F 2002/0852* (2013.01); *A61F 2002/0876* (2013.01); *A61F 2002/0882* (2013.01)

(58) Field of Classification Search
CPC .................. A61B 17/0401; A61B 2017/0404; A61B 2017/0458; A61F 2/0811; A61F 2002/0817; A61F 2002/0847; A61F 2002/0852; A61F 2002/087; A61F 2002/0876; A61F 2002/0882; A61F 2002/0829

USPC ..................... 606/232, 60, 80, 228–231, 300; 623/13.11–13.14, 11.11

See application file for complete search history.

(56) References Cited

U.S. PATENT DOCUMENTS

| | | | |
|---|---|---|---|
| 5,139,520 A * | 8/1992 | Rosenberg | 606/87 |
| 5,211,647 A | 5/1993 | Schmieding | |
| 5,306,301 A | 4/1994 | Graf et al. | |
| 5,320,626 A | 6/1994 | Schmieding | |
| 5,374,269 A * | 12/1994 | Rosenberg | 606/80 |
| 5,645,588 A | 7/1997 | Graf et al. | |
| 5,665,112 A | 9/1997 | Thal | |
| 5,769,894 A | 6/1998 | Ferragamo | |
| 5,891,168 A | 4/1999 | Thal | |
| 6,045,574 A | 4/2000 | Thal | |
| 6,056,752 A | 5/2000 | Roger | |
| 6,193,754 B1 | 2/2001 | Seedhom | |
| 6,267,767 B1 * | 7/2001 | Strobel et al. | 606/104 |
| 6,517,578 B2 | 2/2003 | Hein | |
| 6,533,802 B2 | 3/2003 | Bojarski et al. | |

(Continued)

FOREIGN PATENT DOCUMENTS

| | | |
|---|---|---|
| EP | 1 504 773 A1 | 2/2005 |
| WO | WO-98/12992 A1 | 4/1998 |

(Continued)

*Primary Examiner* — Julian W Woo
*Assistant Examiner* — Christopher L Templeton
(74) *Attorney, Agent, or Firm* — Dickstein Shapiro LLP

(57) ABSTRACT

A technique and reconstruction system for ligament repair employing a continuous loop/button construct. The button has an oblong configuration and is provided with at least one inside eyelet that allows the passage of the continuous loop, preferably a suture loop. The continuous loop/button construct of the present invention may be used for fixation of bone to bone, or of soft tissue to bone.

16 Claims, 11 Drawing Sheets

(56) References Cited

U.S. PATENT DOCUMENTS

| | | |
|---|---|---|
| 6,716,234 B2 | 4/2004 | Grafton et al. |
| 7,500,983 B1 * | 3/2009 | Kaiser et al. ............ 606/232 |
| 7,572,275 B2 * | 8/2009 | Fallin et al. ............ 606/232 |
| 2003/0065361 A1 | 4/2003 | Dreyfuss |
| 2004/0199166 A1 | 10/2004 | Schmieding et al. |
| 2005/0038427 A1 | 2/2005 | Perriello et al. |
| 2005/0065533 A1 | 3/2005 | Magen et al. |
| 2005/0277961 A1 * | 12/2005 | Stone et al. ............ 606/151 |
| 2007/0270857 A1 * | 11/2007 | Lombardo et al. ............ 606/72 |
| 2008/0287991 A1 | 11/2008 | Fromm |

FOREIGN PATENT DOCUMENTS

| | | |
|---|---|---|
| WO | WO-01/91670 A1 | 12/2001 |
| WO | WO 2002/091959 | 11/2002 |

* cited by examiner

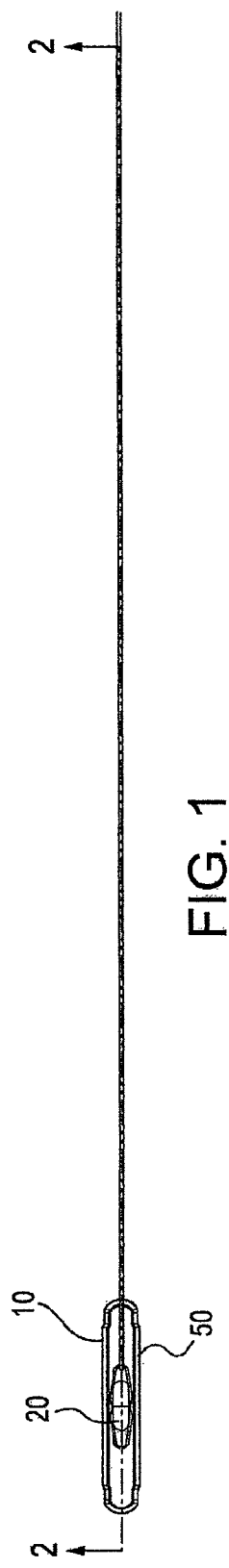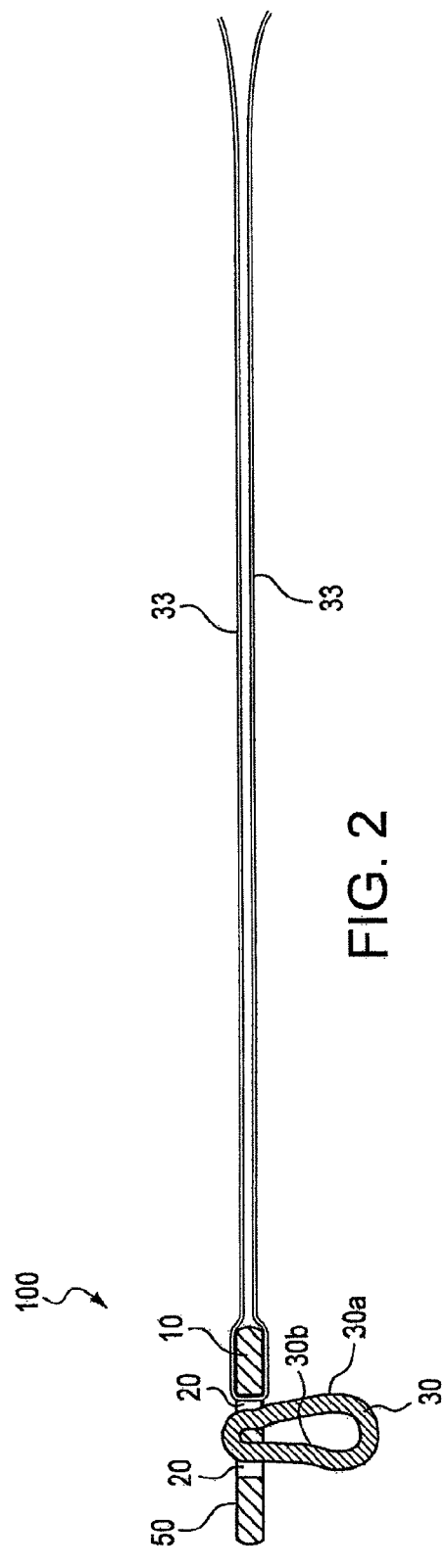

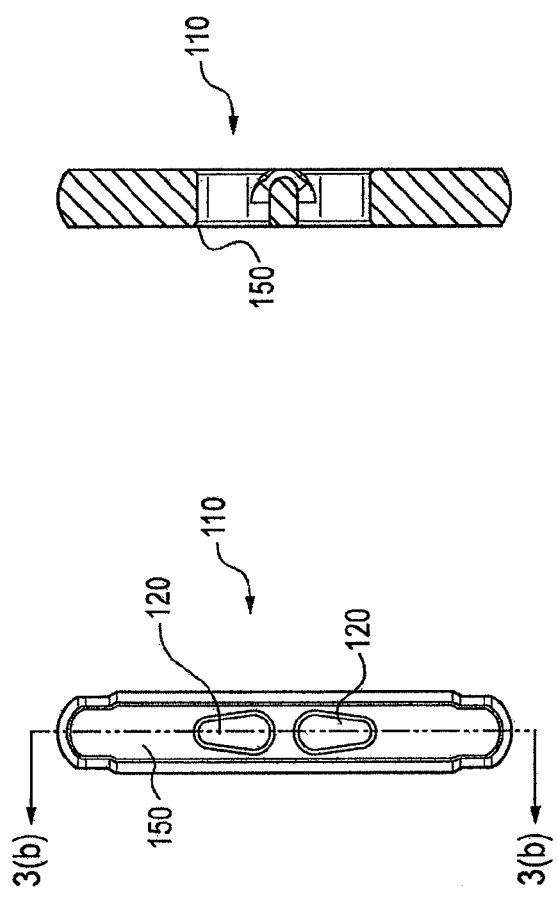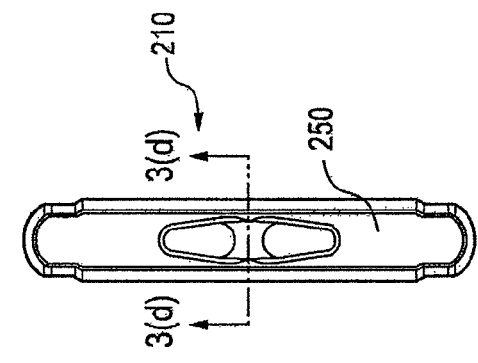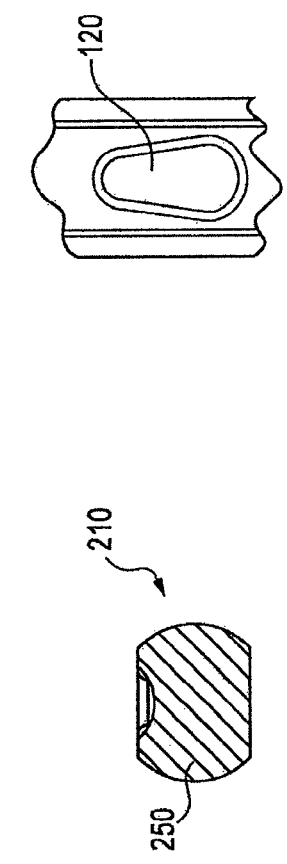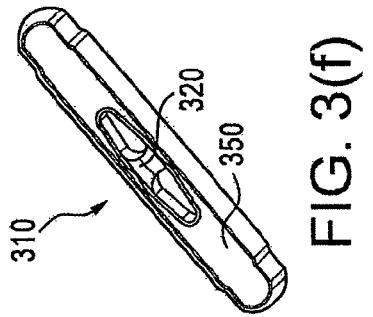

BUTTON AND CONTINUOUS LOOP FOR FIXATION OF LIGAMENTS

CROSS-REFERENCE TO RELATED APPLICATIONS

This application claims the benefit of U.S. Provisional Application No. 60/837,937, filed Aug. 16, 2006, the entire disclosure of which is incorporated by reference herein.

FIELD OF THE INVENTION

The present invention relates to the field of surgery and, more particularly, to a button and continuous loop for fixation of ligaments in reconstructive surgeries.

BACKGROUND OF THE INVENTION

Reconstructive surgeries, particularly anterior cruciate ligament (ACL) reconstruction, are well-known in the art. Methods of ACL reconstruction using interference screw fixation are described, for example, in U.S. Pat. Nos. 5,211,647 and 5,320,626. In general, these methods of tenodesis involve drilling a tunnel through the tibia, drilling a closed tunnel (socket) into the femur, inserting a substitute ACL graft into the tunnels, and securing the grafts to the walls of the tibial and femoral tunnels using interference screws or the like.

The device and method of ligament reconstruction of the present invention provide an alternative fixation technique that does not require the use of interference screws, but instead employs a button with a continuous suture loop for improved fixation.

BRIEF SUMMARY OF THE INVENTION

The present invention provides a technique and reconstruction system for ligament repair. The system of the present invention comprises a continuous loop/button construct used for fixation of bone to bone, or of soft tissue to bone. The button has an oblong configuration and is provided with at least one inside eyelet that allows the passage of the continuous loop, preferably a suture loop. The continuous loop/button construct of the present invention may be used for fixation of bone to bone, or of soft tissue to bone.

Other features and advantages of the present invention will become apparent from the following description of the invention which refers to the accompanying drawings.

BRIEF DESCRIPTION OF THE DRAWINGS

FIG. 1 illustrates a top view of a button according to a first embodiment of the present invention.

FIG. 2 illustrates a cross-sectional view of a continuous loop/button construct employing the button of FIG. 1.

FIG. 3(a) illustrates a top view of a button according to a second embodiment of the present invention.

FIG. 3(b) illustrates a cross-sectional view of the button of FIG. 3(a).

FIG. 3(c) illustrates a top view of a button according to a third embodiment of the present invention.

FIG. 3(d) illustrates a cross-sectional view taken along line B-B of the button of FIG. 3(c).

FIG. 3(e) illustrates an enlarged top view of an eyelet of the button of FIG. 3(a).

FIG. 3(f) illustrates a perspective view of a button according to a fourth embodiment of the present invention.

DETAILED DESCRIPTION OF THE INVENTION

Figure 4:
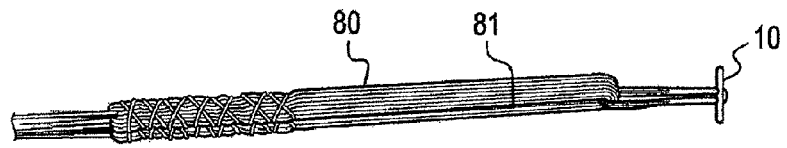
FIGS. 4-9 illustrate various steps of a method of ACL reconstruction employing the continuous loop/button construct of FIG. 2 and according to an embodiment of the present invention.

The present invention provides a technique and reconstruction system for ligament or tendon repair. The system of the present invention comprises a continuous loop/button construct used for fixation of bone to bone, or of soft tissue to bone. The button has an oblong configuration and is provided with an inside eyelet that allows the passage of the continuous loop, preferably a suture loop. The button may be formed, for example, of titanium, PEEK, PLLA or polyethylene. The suture may be a single high strength suture such as FiberWire® suture, sold by Arthrex, Inc. of Naples, Fla., or may be formed of a plurality of suture strands configured to separate from a single strand to a plurality of strands in the continuous loop. The continuous loop/button construct of the present invention may be used for fixation of bone to bone, or of soft tissue to bone.

Referring now to the drawings, where like elements are designated by like reference numerals, FIGS. 1-3 and FIG. 13 illustrate various embodiments of a continuous loop/button construct 100, 200 of the present invention provided with a button 10, 110, 210, 310 preferably of titanium or titanium alloy, or of polyethylene, and a continuous loop 30, 230 preferably of FiberWire® which is attached to the button. In an exemplary embodiment only, the button 10, 110, 210, 310 is formed of polyethylene, and the continuous loop 30, 230 is formed of FiberWire®. In another exemplary embodiment, the button 10, 110, 210, 310 is formed of titanium or titanium alloy, and the continuous loop 30, 230 is formed of FiberWire®.

As shown in the drawings, the button of the present invention preferably has a body 50, 150, 250, 350 with an exemplary oblong configuration and a width that is preferably less than about 1 mm narrower than the width of the drill hole through which the button is inserted and subsequently passed through. The button is provided with at least one inside opening or eyelet 20, 120 (preferably two inside eyelets or openings) that allows the passage of the continuous loop. In the embodiments shown in FIGS. 1, 2 and 3(a)-(c), the button is provided with two eyelets or openings 20, 120 that have a specific configuration to allow the passage of continuous loop 30, 230 (preferably a suture loop). The eyelets may be circular, oblong, elliptical, or may have any other configuration, as desired. For example, FIG. 3(e) illustrates an exemplary configuration for at least one of the two eyelets 120 of button 110 of FIG. 3(a). FIG. 3(f) illustrates an additional configuration for single eyelet 320 of button 310.

Preferably, body 50, 150, 250, 350 of the button of the present invention has a length of about 10 mm to about 20 mm, more preferably of about 12 mm to about 15 mm, and a width that is less than about 1 mm narrower than the width of the drill hole through which the button is inserted and subsequently passed through. Preferably, button 10 is very small, having a width that allows it to pass through a 3 mm cortical pin hole without over drilling, which in turn saves time and preserves bone.

Figure 13:
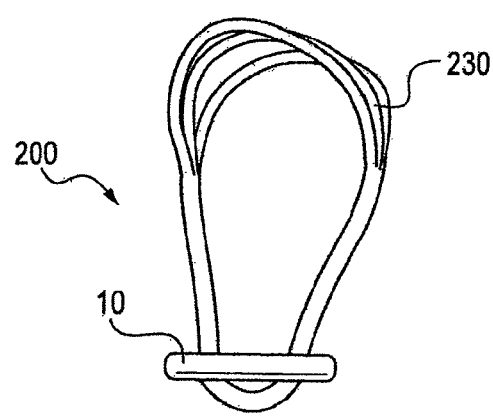
FIG. 13 illustrates a continuous loop/button construct employing the suture loop of FIG. 12 and in accordance with an embodiment of the present invention.

As shown in FIGS. 2 and 13, the button is provided with at least an inside eyelet 20 that allows the passage of continuous loop 30, 230 (preferably a suture loop). In an exemplary embodiment, the suture loop may be a single high strength suture such as FiberWire® suture, sold by Arthrex, Inc. of Naples, Fla., and described in U.S. Pat. No. 6,716,234, the disclosure of which is incorporated by reference herein. FiberWire suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The FiberWire suture may include a core within a hollow braided construct, the core being a twisted yarn of UHMWPE. The suture may optionally include filaments of various colors.

The continuous loop may be available in various lengths and may comprise various materials such as nitinol or suture, preferably a high-strength suture material, or combinations of such materials. Preferably, the suture loop is the equivalent of about three #5 FiberWire® suture strands, with a wide atraumatic graft interface to protect the graft integrity.

Figure 12:
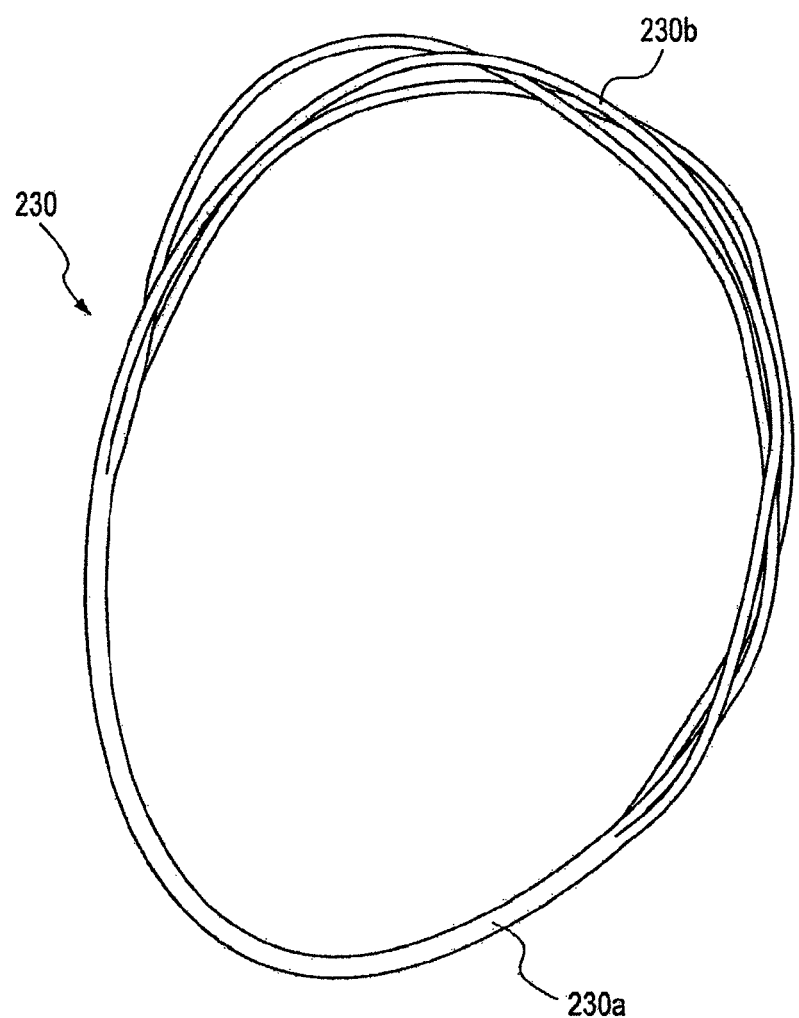
FIG. 12 illustrates a continuous suture loop which transitions from one strand to three strands.

In another exemplary embodiment, and as shown in FIGS. 12 and 13, the continuous loop 230 may be formed of a plurality of suture strands configured to separate from a single strand to a plurality of strands in a continuous loop. For example, the continuous loop 230 comprises a braided strand 230a of suture (such as FiberWire®, for example) that is configured to trifurcate from one single strand to three strands 230b, as shown in FIG. 12. In this exemplary "three strand" design, the continuous loop is configured to pass through the button component at the single strand section of the loop, as shown in FIG. 13.

In additional embodiments, the continuous loop of the present invention may include suture filaments of various colors. For example, suture loop 30 of FIG. 2 is a braided ultrahigh molecular weight polyethylene (UHMWPE) three-strand loop of white color (30a) which may optionally include blue filaments (30b) and which may be optionally coated with a silicon elastomer, for example, prior to the formation of the loop. The loop may be formed by stitching ends of a suture strand initially inserted through the opening or eyelet 20 of the button, to form a stitched region of the loop which ends below the button (for example, a minimum of 8 mm below the bottom surface of the button) to reduce the assembly profile when pulled taught. The suture loop/button construct 100, 200 of the present invention is preferably used in conjunction with passing sutures 33 (FIG. 2) that also pass through eyelet 20.

The system of the present invention may be employed for fixation of bone to bone, or for fixation of soft tissue to bone. In an exemplary embodiment, the continuous loop/button construct 100, 200 of the present invention is used to secure a soft tissue graft in a bone socket in a retrograde manner, for example. According to another exemplary embodiment, the continuous loop/button construct 100, 200 of the present invention is used to secure a bone-to-bone (BTB) graft in a femoral tunnel or socket in a retrograde manner, for example. The bone socket or tunnel may be formed by a conventional (antegrade manner) or by a retrograde manner (for example, by employing a retrodrill cutter).

In these particular and only exemplary embodiments, a method of ACL reconstruction using the continuous loop/button construct 100, 200 comprises, for example, the steps of: (i) drilling a femoral tunnel or socket in an antegrade manner, or retrograde manner (using a retrodrill cutter which is inserted in a retrograde manner through the femur); (ii) securing a graft (soft tissue graft or BTB graft) to the continuous loop/button construct 100, 200 of the present invention; (iii) passing the graft with the button through the femoral tunnel; and (iv) securing the button to the femoral cortex once the button exits the femoral socket.

Figure 9:
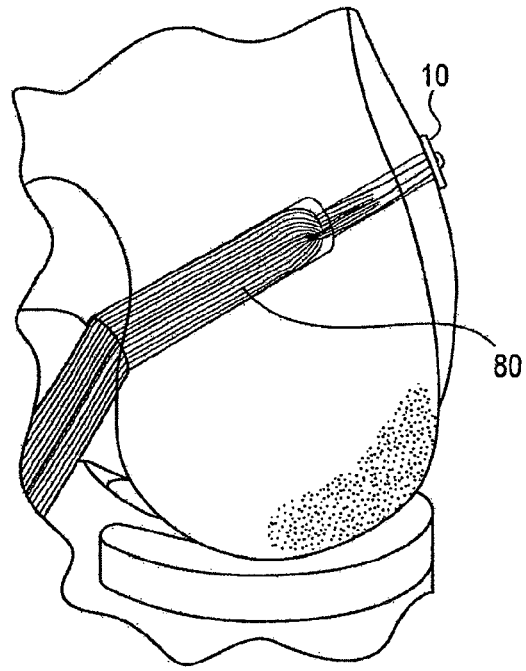

The exemplary technique of ACL reconstruction detailed above is further described below with reference to FIGS. 5-8 (for soft tissue graft) and with reference to FIGS. 9 and 10 (for BTB graft).

Figure 5:
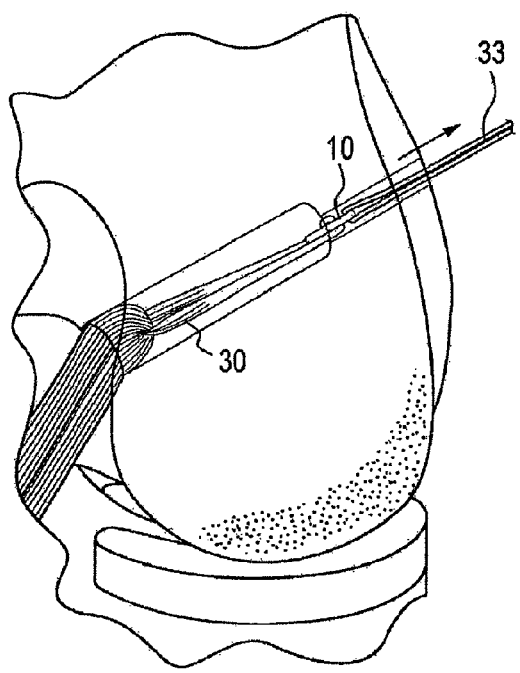
Figure 5A:
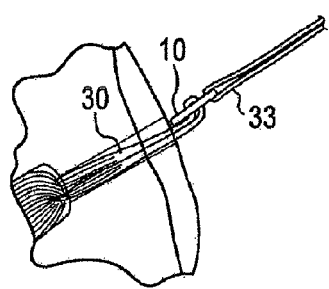
Figure 5B:
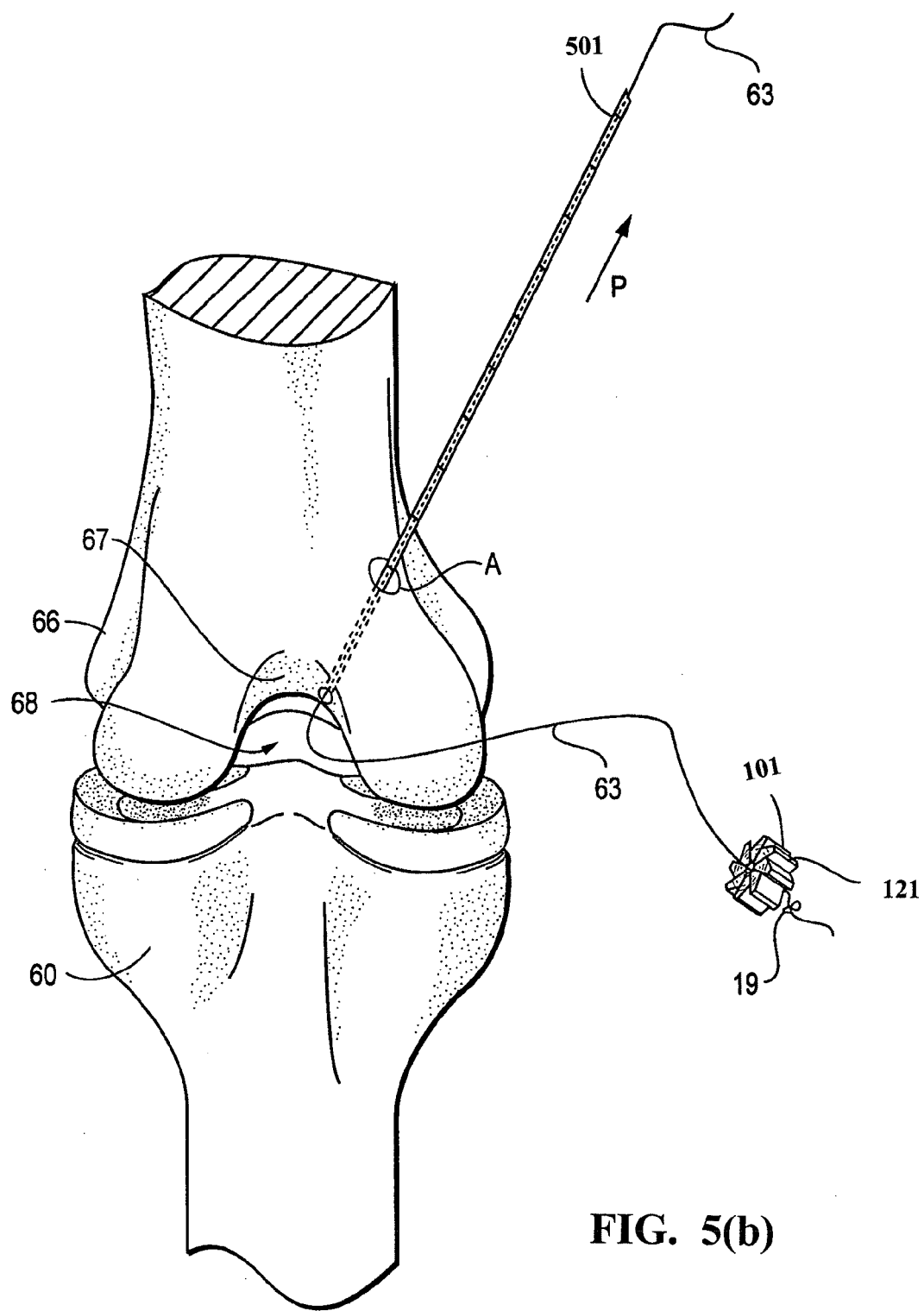
Figure 5C:
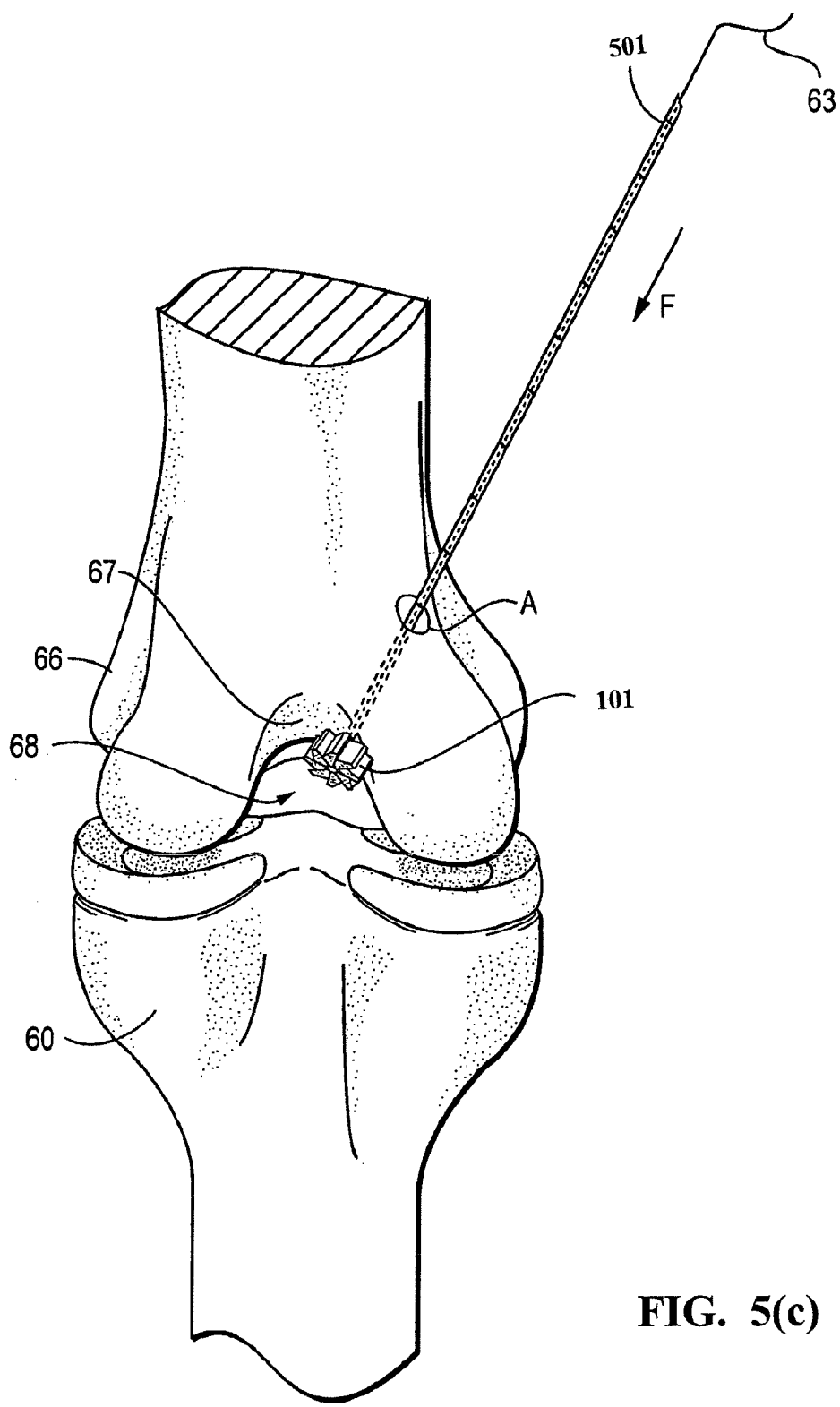
Figure 5D:
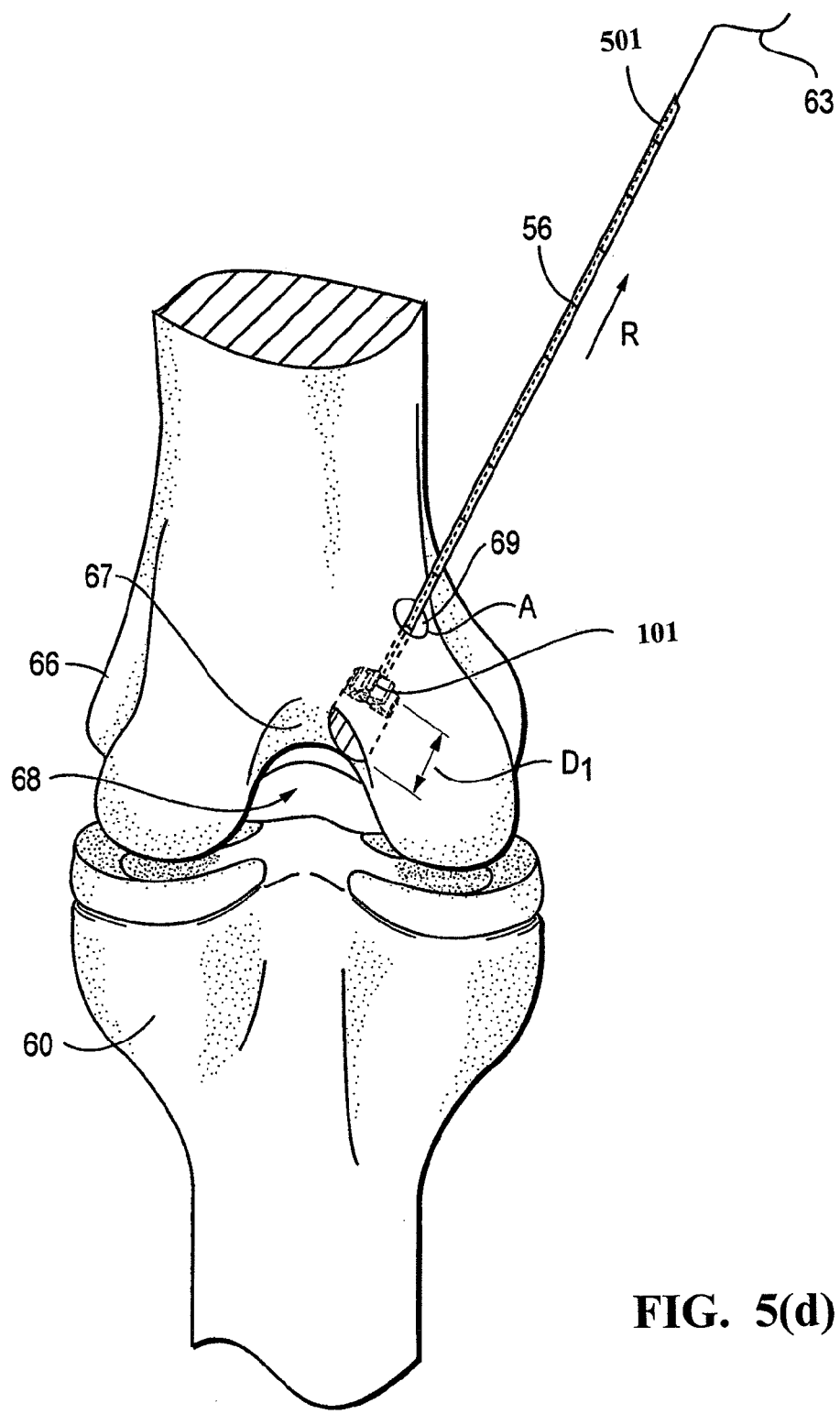
Figure 5E:
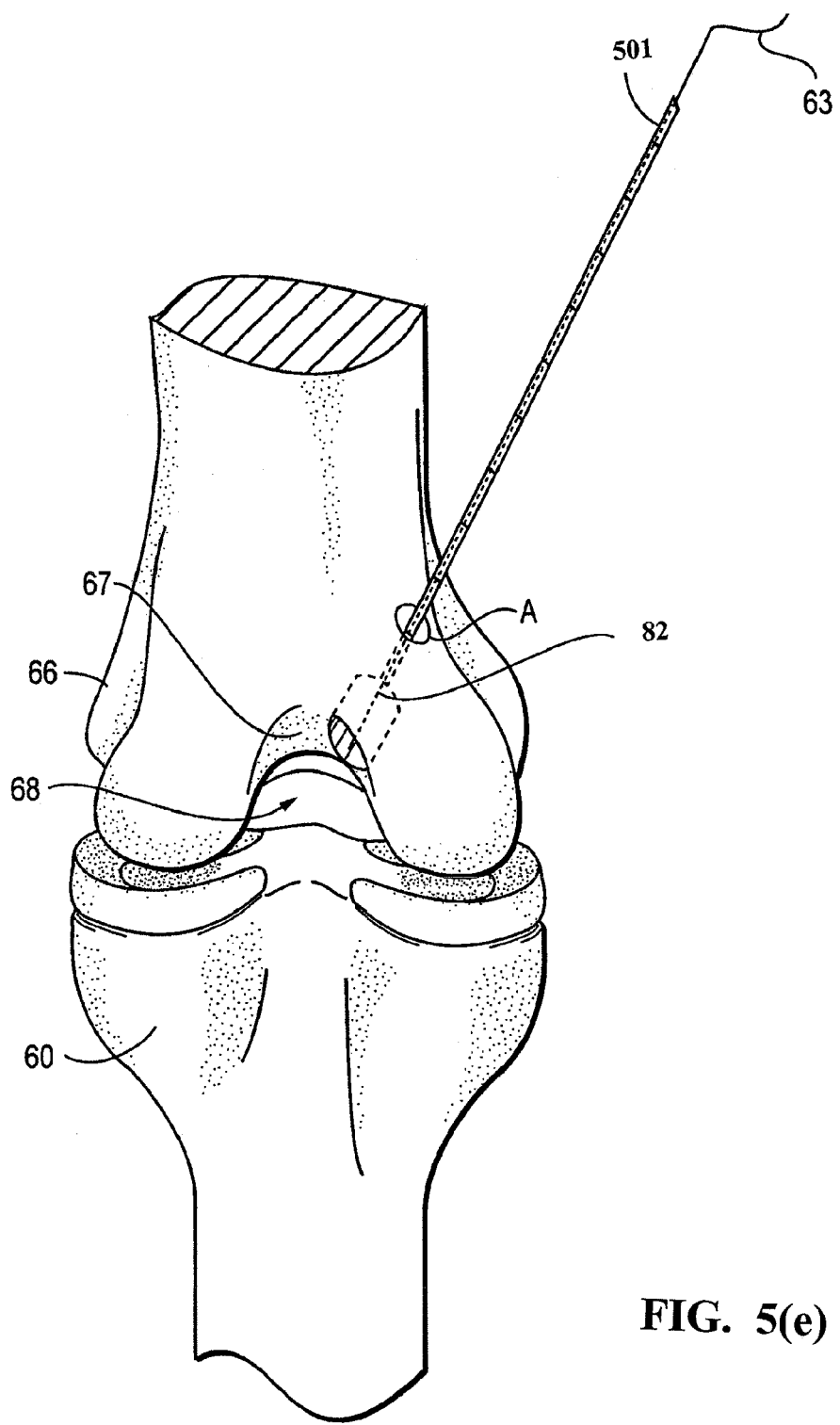
Figure 6:
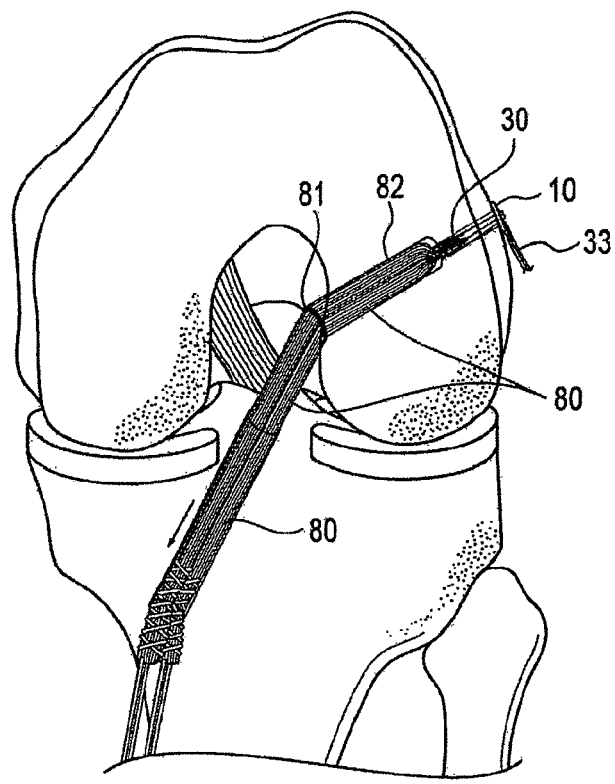
Figure 7:
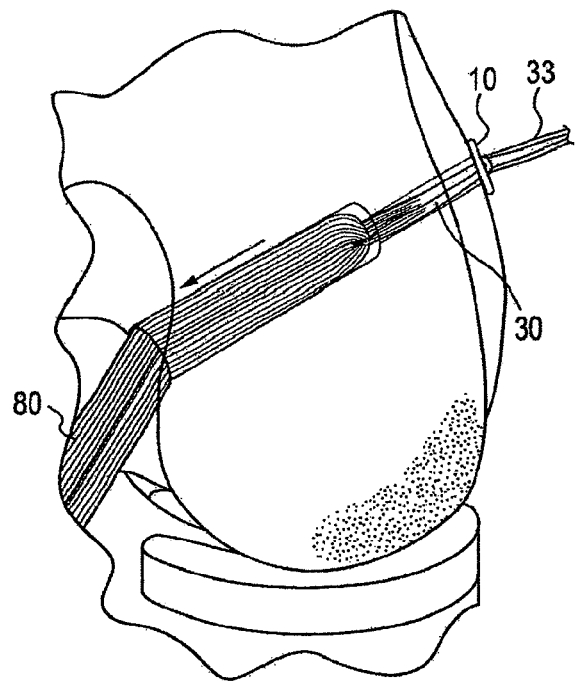
Figure 8:
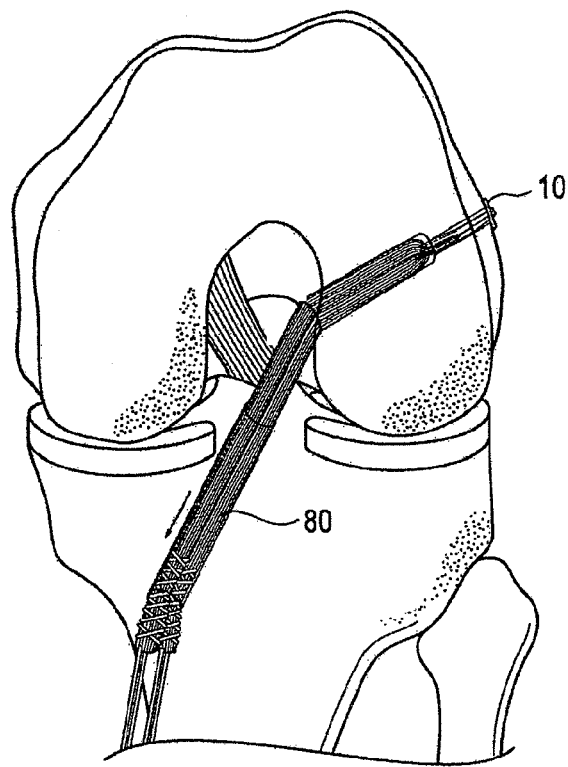

According to one embodiment of the present invention, and with reference to FIGS. 5(*b*)-5(*e*), a femoral socket 82 is prepared in femur 66 (which articulates with tibia 60) by employing a retrodrill device provided with a retrodrill cutter 101 detachable from a retrodrill guide pin 501, in the manner described in U.S. Patent Application Publication No. 2004/0199166, entitled "ACL Reconstruction Technique Using Retrodrill," the disclosure of which is hereby incorporated by reference herein in its entirety.

As described in U.S. Patent Application Publication No. 2004/0199166, a retrodrill device for ACL reconstruction is provided with a retrodrill cutter 101 detachable from a retrodrill guide pin 501. The retrodrill cutter 101 is inserted in a retrograde manner through the femur 66 by employing a retrodrill guide pin provided with depth markings Once the proper anatomical position in the joint for creating a femoral socket has been located, the marking hook of a drill guide is placed through the antero-medial portal and inserted in an "over-the-top" position according to an outside-in technique. The retrodrill guide pin 501 is then inserted into the sleeve of the drill guide and drilled through the lateral femur until contact is made with a marking hook of the drill guide. The retrodrill cutter 101 is then placed into the anatomical joint space 68 (FIG. 5(*b*)) through the antero-medial portal, using a strand 63 placed through a cannula of the retrodrill cutter 101 and retained using a Mulbery knot 19 tied in the strand. The strand in pulled in the direction of arrow "P" of FIG. 5(*b*) to draw the retrodrill cutter 101 through the medial portal and into the joint space 68. The retrodrill cutter 101 is positioned to be threaded onto the retrodrill guide pin 501 by turning and advancing the retrodrill pin 501 in the relative direction of arrow "F" (FIG. 5(*c*)) (antegrade) into the cannulation of the retrodrill cutter 101. Once secured within the retrodrill cutter 101, the retrodrill guide pin 501 is retracted in a retrograde manner until the retrodrill cutter contacts the femoral intercondylar notch 67 (FIG. 5(*c*)). The proximal end of the retrodrill guide pin is coupled to a drill. The retrodrill cutter is then rotated and retracted into the lateral femur to the proper depth D1 (FIG. 5(*d*)) as measured on the outside of the knee by the depth markings on the retrodrill guide pin. After the femoral socket 82 (FIG. 5(*e*) is formed in this manner, the retrodrill cutter 101 is removed from the retrodrill guide pin 501 by applying a reversed drilling motion (in the direction of arrow "R" of FIG. 5(*d*)) to the guide pin while grasping the cutter.

Formation of a tibial tunnel or socket by the method described above or by a conventional method may be carried out before or after the formation of the femoral socket.

Once the femoral and tibial tunnels or sockets have been completed, graft insertion and fixation may be subsequently carried out. According to an exemplary embodiment of the present invention, and as illustrated in FIGS. 4-9, graft 80 which may be a soft tissue graft is folded in half over the loop 30 of the button 10 and tension is applied. A sterile marker may be employed to draw a line 81 on the graft, the line indicating a distance that equals the length of the femoral socket or tunnel plus about 6 mm (if using a 12 mm button) or about 8 mm (if using a 15 mm button), for example, from the looped end of the graft. This mark 81 will be used to indicate when the button 10 has exited the femoral tunnel or socket.

Subsequently, passing sutures 33 are pulled and graft 80 is passed into femoral tunnel or socket 82. When the line 81 marked on the graft 80 reaches the opening of the femoral socket or tunnel 82 on the femoral cortex, a slight popping sensation may be felt as the button 10 exits and begins to flip horizontally on the femoral cortex (FIGS. 7-10). Distal traction on the graft and release of the passing sutures facilitate complete deployment of the button. The passing suture 33 may be removed and tibial fixation may be completed.

Figure 11:
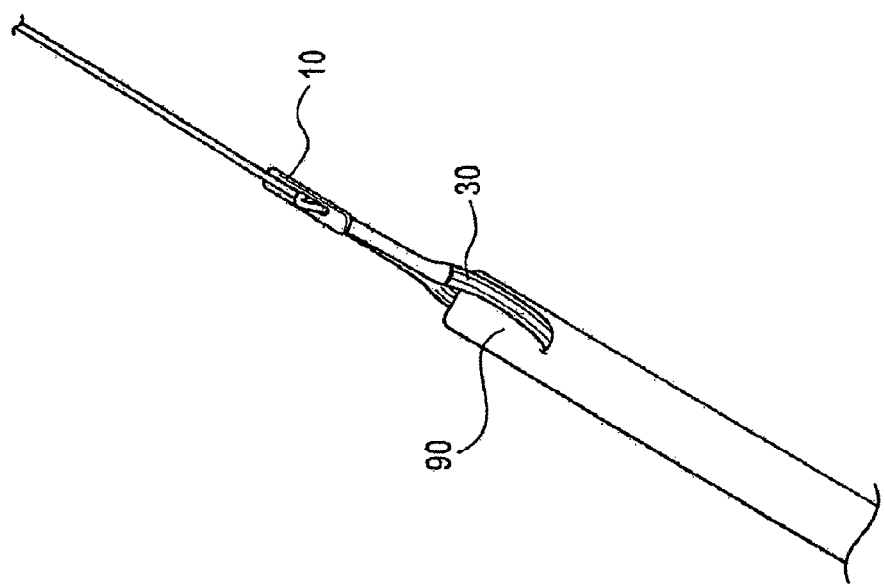
FIG. 11 illustrates the continuous loop/button construct of FIG. 2 used for BTB fixation and according to another embodiment of the present invention.
Figure 10:
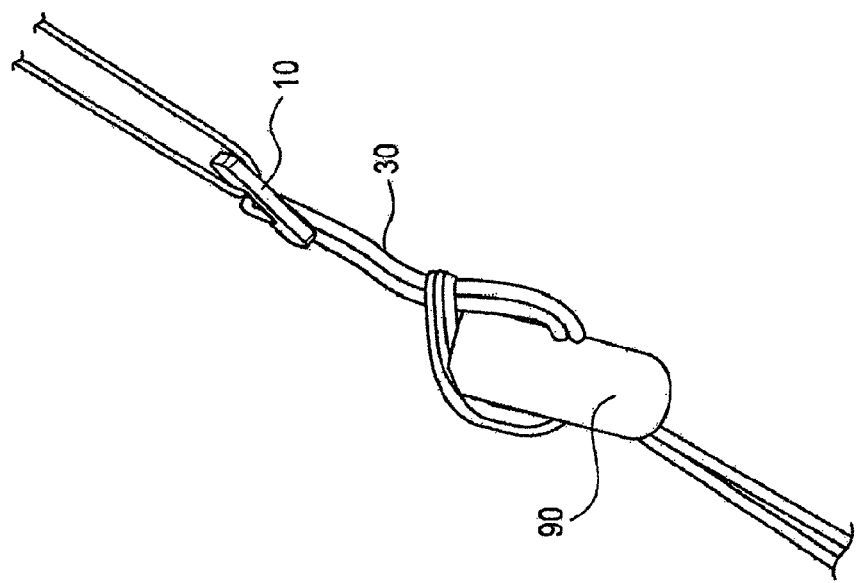
FIG. 10 illustrates the continuous loop/button construct of FIG. 2 used for BTB fixation and according to an embodiment of the present invention.

FIGS. 10 and 11 illustrate a BTB graft 90 which is secured within a femoral tunnel by employing the continuous loop/button construct 100 of the present invention. BTB graft 90 is secured within the femoral tunnel in a manner similar to that described above with reference to the soft tissue graft 80. The femoral tunnel is formed preferably in a retrograde manner and the continuous loop/button construct 100 is also preferably inserted in a retrograde manner.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed as new and desired to be protected by Letters Patent of the United States is:

1. A method of positioning tissue within the body, comprising the steps of:
   providing a suture loop/button construct having a continuous suture loop and a button attached to the continuous suture loop, the button having a body and two eyelets extending through opposing surfaces of the body, the continuous suture loop being attached to the button by passage of the continuous loop through the two eyelets, and a single passing suture, wherein the single passing suture is passed through only one of the two eyelets;
   providing the suture loop/button construct in the vicinity of tissue to be positioned;
   attaching the tissue to be positioned to the continuous suture loop of the suture loop/button construct by folding the tissue to be positioned over the continuous suture loop;
   inserting and passing the suture loop/button construct with the attached tissue to be positioned, and pulling the suture loop/button construct with the attached tissue to be positioned through a socket or a tunnel in a bone, using only the single passing suture passed through only one of the two eyelets, the button having a length of about 10 mm to about 20 mm and a width that is about 1 mm narrower than a width of the socket or the tunnel through which the button is inserted and passed through, the passing suture single passing the folded tissue to be positioned into the socket or the tunnel in the bone, the button exiting the socket or the tunnel and beginning to flip horizontally as it exits cortical bone; and
   facilitating complete deployment of the button by distal traction on the folded tissue to be positioned and release of the single passing suture such that the button is secured on an outside surface of the bone and thereby secures the attached tissue to be positioned within the socket or tunnel.

2. The method of claim 1, wherein the tissue to be positioned is biological or non-biological tissue.

3. The method of claim 1, wherein the tissue to be positioned is selected from the group consisting of a ligament, tendon, bone and cartilage.

4. The method of claim 1, wherein the tissue to be positioned is a soft tissue graft or a BTB graft.

5. The method of claim 1, wherein the continuous suture loop comprises a first portion formed of a single suture strand and a second portion formed of a plurality of suture strands.

6. A method of conducting arthroscopic surgery, comprising the steps of:
   forming a bone tunnel or socket;
   providing a suture loop/button construct in the vicinity of the bone tunnel or socket, the suture loop/button construct comprising a button having two eyelets, a continuous suture loop attached to the button by passage of the continuous loop through the two eyelets, the continuous suture loop comprising a first portion formed of a single suture strand and a second portion which furcates from the single suture strand to a plurality of single suture strands, and a passing suture passed through one of the two eyelets;
   attaching a graft to the continuous suture loop of the suture loop/button construct by folding the graft in half over the continuous suture loop;
   subsequently inserting the graft attached to the suture loop/button construct into the bone tunnel or socket and passing the suture loop/button construct through the bone tunnel or socket by pulling the suture loop/button construct with the attached graft using only the passing suture passed through only one of the two eyelets, the passing suture passing the folded graft into the bone tunnel or socket, the button beginning to flip horizontally as it exits cortical bone; and
   facilitating complete deployment of the button by distal traction on the folded graft and release of the passing suture such that the button is secured on an outside surface of the bone, thereby securing the graft within the bone tunnel or socket.

7. The method of claim 6, wherein the graft is a soft tissue graft or a BTB graft.

8. The method of claim 6, wherein the bone tunnel or socket is a femoral or tibial bone tunnel or socket.

9. The method of claim 6, wherein the suture loop is formed of a suture material comprising ultrahigh molecular weight polyethylene.

10. The method of claim 6, wherein the button has an oblong configuration.

11. The method of claim 6, wherein the button has a length of 10 to 20 mm.

12. The method of claim 6, wherein the button has a width that is less than 1 mm narrower than a width of the bone tunnel or socket.

13. The method of claim 6, wherein the bone tunnel or socket is formed in a retrograde manner using a rotary drill cutter.

14. The method of claim 13, wherein the rotary drill cutter comprises two opposed sides provided with cutting surfaces on both sides.

15. The method of claim 14, wherein the rotary drill cutter is configured for cutting in two opposite directions.

16. A method of knee ligament reconstruction, comprising the steps of:
forming a first socket in femur by conducting a retrograde drilling using a rotary drill cutter;
forming a second socket in tibia by conducting a second action using the rotary drill cutter;
providing a suture loop/button construct in the vicinity of the first and second sockets, the suture loop/button construct comprising a button with two eyelets, a continuous suture loop attached to the button by passage of the continuous loop through the two eyelets, and a passing suture passed through only one of the two eyelets, wherein the continuous suture loop comprises a first portion formed of a single suture strand and a second portion which furcates from the single suture strand to a plurality of suture strands;
attaching a graft to the suture loop of the suture loop/button construct by folding the graft in half over the suture loop;
pulling the suture loop/button construct with the attached graft through the first socket using only the passing suture passed through one of the two eyelets, the passing suture passed through only one of the two eyelets, the button beginning to flip horizontally as it exits cortical bone abutting the first socket;
facilitating complete deployment of the button by distal traction on the folded graft and release of the passing suture such that the button is secured on an outside surface of the cortical bone abutting the first socket and thereby secures the attached graft within the first socket; and
securing the graft within the second socket.

\* \* \* \* \*